(12) United States Patent
Pelley

(10) Patent No.: US 9,795,518 B2
(45) Date of Patent: Oct. 24, 2017

(54) METHOD OF SHAPING A TAMPON FOR FEMININE HYGIENE

(71) Applicant: Johnson & Johnson GmbH, Neuss (DE)

(72) Inventor: Kenneth A. Pelley, Hopewell, NJ (US)

(73) Assignee: Johnson & Johnson GmbH, Neuss (DE)

( * ) Notice: Subject to any disclaimer, the term of this patent is extended or adjusted under 35 U.S.C. 154(b) by 0 days.

(21) Appl. No.: 15/452,815

(22) Filed: Mar. 8, 2017

(65) Prior Publication Data

US 2017/0172811 A1 Jun. 22, 2017

Related U.S. Application Data

(62) Division of application No. 14/540,671, filed on Nov. 13, 2014, now Pat. No. 9,622,919.

(51) Int. Cl.
*B29C 43/02* (2006.01)
*A61F 13/20* (2006.01)
(Continued)

(52) U.S. Cl.
CPC .... *A61F 13/2088* (2013.01); *A61F 13/15747* (2013.01); *A61F 13/2037* (2013.01);
(Continued)

(58) Field of Classification Search
None
See application file for complete search history.

(56) References Cited

U.S. PATENT DOCUMENTS 3,854,481 A 12/1974 Messing
4,212,301 A 7/1980 Johnson
(Continued)

FOREIGN PATENT DOCUMENTS

EP 1459720 A1 9/2004
EP 1459720 B1 4/2005
(Continued)

OTHER PUBLICATIONS

International Search Report dated Jan. 27, 2016, Application No. PCT/US2015/060098.

*Primary Examiner* — Edmund Lee

(57) ABSTRACT

A process of forming a shaped, dimensionally stable tampon includes the steps of: radially compressing a tampon blank to form a dimensionally stable intermediate pledget having an intermediate pledget diameter and a longitudinal axis; placing the intermediate pledget into a hollow carrier and inserting the intermediate pledget and hollow carrier into a mold; urging the intermediate pledget into the mold via a ram bearing on an end of the intermediate pledget contained within the hollow carrier and withdrawing the hollow carrier from the mold to permit the exposed end of the intermediate pledget to substantially fill the mold and to form the shaped, dimensionally stable tampon; removing the shaped, dimensionally stable tampon from the mold; and enclosing the shaped, dimensionally stable tampon in a primary package that conforms to the shape thereof. The mold has an access opening through which the hollow carrier can be withdrawn.

8 Claims, 15 Drawing Sheets

(51) Int. Cl.
*A61F 13/15* (2006.01)
*A61F 13/551* (2006.01)
*B29C 43/18* (2006.01)
*B65B 5/04* (2006.01)
*B65B 63/02* (2006.01)
*B29L 31/00* (2006.01)
*B29C 43/34* (2006.01)

(52) U.S. Cl.
CPC ...... *A61F 13/55175* (2013.01); *B29C 43/027* (2013.01); *B29C 43/184* (2013.01); *B65B 5/04* (2013.01); *B65B 63/02* (2013.01); *A61F 2013/15715* (2013.01); *B29C 2043/029* (2013.01); *B29C 2043/3405* (2013.01); *B29L 2031/769* (2013.01)

(56) References Cited

U.S. PATENT DOCUMENTS

| | | | |
|---|---|---|---|
| 4,627,849 A | | 12/1986 | Walton et al. |
| 5,153,971 A | * | 10/1992 | Van Iten ............ A61F 13/2085 28/118 |
| 5,659,934 A | | 8/1997 | Jessup et al. |
| 6,310,269 B1 | | 10/2001 | Friese et al. |
| 7,736,572 B2 | * | 6/2010 | Gilbert ............... A61F 13/2085 264/107 |
| 7,740,787 B2 | * | 6/2010 | Hubbard, Jr. ...... A61F 13/2085 264/313 |
| 7,867,209 B2 | | 1/2011 | Jorgensen et al. |
| 7,981,347 B2 | * | 7/2011 | Hubbard, Jr. ...... A61F 13/2085 264/313 |
| 8,082,639 B2 | | 12/2011 | Rolli |
| 8,293,968 B2 | | 10/2012 | Schmidt-Först et al. |
| 8,460,262 B2 | | 6/2013 | Fung et al. |
| 8,518,005 B2 | | 8/2013 | Handel et al. |
| 8,735,647 B2 | | 5/2014 | Schoelling |
| 8,827,975 B2 | | 9/2014 | Kimball et al. |
| 8,834,439 B2 | | 9/2014 | Kimball et al. |
| 2003/0176845 A1 | | 9/2003 | Kollwitz et al. |
| 2007/0234532 A1 | * | 10/2007 | Gilbert ............... A61F 13/2051 28/118 |
| 2008/0065041 A1 | * | 3/2008 | Stan .................... G06F 17/5018 604/385.18 |
| 2008/0119811 A1 | * | 5/2008 | Gilbert ............ A61F 13/15707 604/385.17 |
| 2008/0275417 A1 | * | 11/2008 | Gilbert ............... A61F 13/2051 604/385.18 |
| 2009/0082712 A1 | | 3/2009 | Hasse et al. |
| 2010/0102481 A1 | * | 4/2010 | Hubbard, Jr. ....... A61F 13/2085 264/318 |
| 2013/0018342 A1 | | 1/2013 | Schmidt-Forst |
| 2013/0072892 A1 | | 3/2013 | Hasse et al. |
| 2014/0000628 A1 | | 1/2014 | Avery, Jr. et al. |

FOREIGN PATENT DOCUMENTS

| | | |
|---|---|---|
| EP | 1622556 B1 | 2/2006 |
| EP | 1601322 B1 | 12/2008 |
| WO | WO2004/080362 A1 | 9/2004 |
| WO | WO2004/100846 A1 | 11/2004 |
| WO | WO2008/056339 A1 | 5/2008 |
| WO | WO2009/040737 A2 | 4/2009 |
| WO | WO2014/004798 A1 | 1/2014 |

* cited by examiner

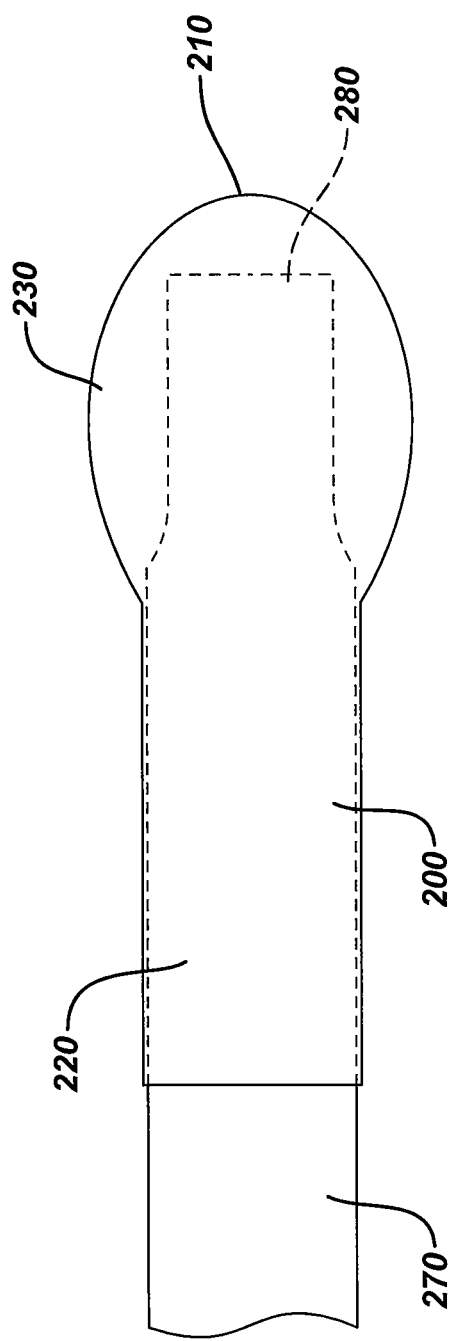

METHOD OF SHAPING A TAMPON FOR FEMININE HYGIENE

This application is a divisional application of U.S. Ser. No. 14/540,671 filed on Nov. 13, 2014, now U.S. Pat. No. 9,622,919, the complete disclosure of which is hereby incorporated herein by reference for all purposes.

FIELD OF THE INVENTION

The present invention relates to a method for forming fibrous tampons having a non-cylindrical shape.

BACKGROUND OF THE INVENTION

Individual absorbent articles for personal hygiene articles are protected from the environment by sheets of material commonly referred to as wrappers or overwrap. Tampons, in particular, have employed wrappers in which each tampon is encased in a separate primary package, which may be then be sold in quantity in secondary packaging often a box. Tampons are generally categorized in two classes: applicator tampons and digital tampons. Applicator tampons are basically tampons contained within an applicator. The applicator may be plastic or cardboard and may include design elements such as finger grips or petals for ease of insertion.

The wrapper for an applicator tampon is typically elongated, loose, and flange or fin sealed at the ends with a small cut or notch at one end which the user uses to tear open the wrapper in a longitudinal fashion.

Digital tampons are basically compressed cylindrical objects and may include a tapered insertion end. As digital tampons are not contained within an applicator, they are typically contained within a wrapper. The wrapper for a digital tampon is typically tight fitting, often contacting the outer surface of the tampon completely about the perimeter and sealed against the tampon at both the insertion and withdrawal end. This tight wrapping may help maintain the shape of the tampon and prevent deformation.

Historically, wrappers have been made from clear types of materials such as plastics (e.g., polypropylene) or cellophane. Since digital tampons typically also contain a cover over the absorbent material, it is sometimes necessary to include a slip agent or an anti-static agent to ensure that the tampon is easily removed from the wrapper and parts of the wrapper does not adhere to the tampon during insertion.

Over the years there have developed many issues with the wrappers for digital tampons. Sometimes the tampon has "relaxed" after compression and is difficult to remove from a wrapper due to the snugness of the fit. Some wrapper materials may actually stick to the outer surface of the tampon and be difficult to remove due to material interaction, causing the user to pry off the overwrap from the tampon. See, for example, WO 2004/080362. Other times, depending on the choice of material for the wrapper, there may be a static charge to the wrapper which causes the pieces of the wrapper to cling to the user's fingers after the wrapper seal has been broken and the tampon removed.

New improvements to digital tampons include shaping the body of the tampon, varying the grooves and providing surface aberrations such as protuberances or depressions. Methods to make these types of shaped or patterned tampons typically involve a split mold cavity, which allows for the tampon to be removed from the mold without disrupting the tampon shape or surface. For shaped tampons that are to be digitally inserted, providing a wrapper to ensure cleanliness can pose a challenge. Shaped tampons may require non-cylindrical wrapping to maintain its shape.

This invention proposes a solution to forming a shaped tampon along with providing a wrapper which provides cleanliness and helps maintain the shape of the tampon during storage.

SUMMARY OF THE INVENTION

Surprisingly, we have found a novel way to provide a shaped, dimensionally stable tampon wherein the desired final tampon shape has a maximum dimension perpendicular to the longitudinal axis that is greater than the largest diameter of an intermediate pledget. In one aspect of the invention, a process of forming a shaped, dimensionally stable tampon includes the steps of: radially compressing a tampon blank to form a dimensionally stable intermediate pledget having an intermediate pledget diameter and a longitudinal axis; forming a shaped primary tampon package having a length, a first, closed end and a second, open end; inserting the intermediate pledget into the shaped primary tampon package, a first portion of the intermediate pledget adjacent the first enlarged portion of the shaped primary tampon package and a second portion of the intermediate pledget adjacent the second portion of the shaped primary tampon package; expanding the first portion of the intermediate pledget to substantially fill the first enlarged portion of the shaped primary tampon package to form the dimensionally stable tampon; and closing the second, open end of the shaped primary tampon package.

In another aspect of the invention, a process of forming a shaped, dimensionally stable tampon includes the steps of: radially compressing a tampon blank to form a dimensionally stable intermediate pledget having an intermediate pledget diameter and a longitudinal axis; placing the intermediate pledget into a hollow carrier and inserting the intermediate pledget and hollow carrier into a mold; urging the intermediate pledget into the mold via a ram bearing on an end of the intermediate pledget contained within the hollow carrier and withdrawing the hollow carrier from the mold such that an exposed end of the intermediate pledget is forced against the mold whereby axial force on the intermediate pledget provides radial expansion from the longitudinal axis of the intermediate pledget to permit the exposed end of the intermediate pledget to substantially fill the mold and to form the shaped, dimensionally stable tampon; removing the shaped, dimensionally stable tampon from the mold; and enclosing the shaped, dimensionally stable tampon in a primary package that conforms to the shape thereof. The mold has an access opening through which the hollow carrier can be withdrawn.

BRIEF DESCRIPTION OF THE DRAWING

FIG. 7 is a side view of the primary tampon package of the embodiment of FIGS. 5-6.

DETAILED DISCUSSION OF THE PREFERRED EMBODIMENTS

A more particular description of the invention, briefly summarized above may be had by reference to the embodiments thereof that are illustrated in the appended drawings. It is to be so noted, however, that the appended drawings illustrate only typical embodiments of the invention and, therefore, are not to be considered limiting of its scope, for the invention may admit to other equally effective embodiments.

Figure 1:
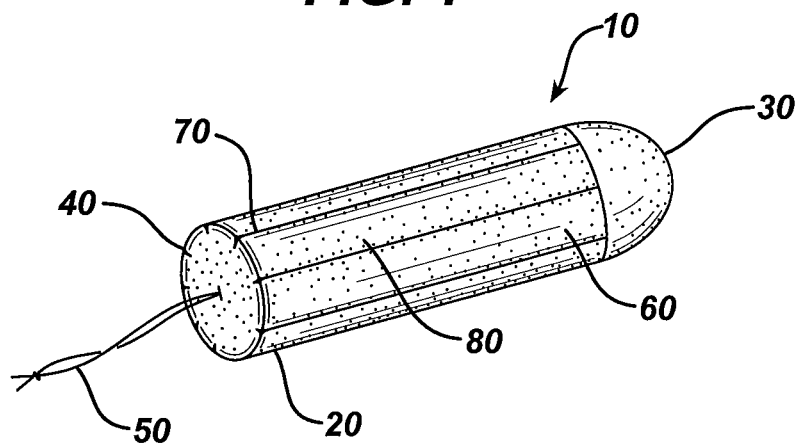
FIG. 1 is a perspective view of a tampon according to the prior art.

Referring to FIG. 1, a radially compressed tampon 10 for feminine hygiene according to the prior art is a generally cylindrical body 20 of compressed fibers having an insertion end 30 and a withdrawal end 40 having extending therefrom a withdrawal string 50. Such a tampon has sufficient dimensional stability to permit insertion into a user's vagina for absorption of menses without requiring an additional applicator. These tampons are often described as digital tampons and may be inserted digitally (through the use of one's fingers, without an applicator). Often, these tampons incorporate an outer fluid-pervious cover 60 and are compressed in a manner that produces a plurality of generally longitudinally extending grooves 70, separated by ribs 80. The grooves may be aligned parallel to a longitudinal central axis as described in Friese et al., U.S. Pat. No. 6,310,269, oriented helically about the outer surface as described in Schoelling, U.S. Pat. No. 8,735,647, or otherwise oriented along the length of the product, such as described in Fung et al., U.S. Pat. No. 8,460,262 B2; Kimball et al., U.S. Pat. Nos. 8,827,975 B2 and 8,834,439 B2; and Hysalma GmbH, EP Pat. No. 1 459 720 B1.

Figure 2:
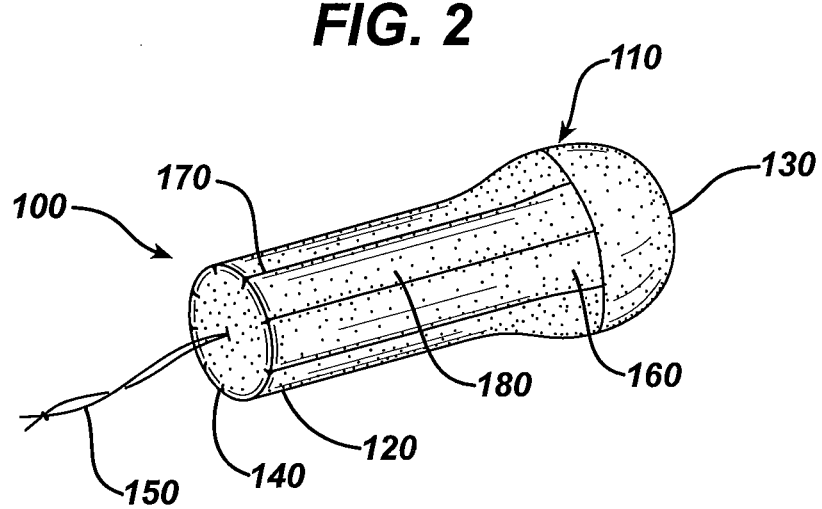
FIG. 2 is a perspective view of a tampon according to the present invention.

We have found that it is possible to transform such prior art tampons into shaped tampons for distribution and sale to consumers. In particular, we have developed a method to shape a tampon 100 for feminine hygiene into a structure having an enlarged portion 110 at one end, thereof. Such a tampon 100 according to the present invention is shown in FIG. 2. This tampon has a body 120 of compressed fibers having an insertion end 130 and a withdrawal end 140 having extending therefrom a withdrawal string 150. Again, this tampon has sufficient dimensional stability to permit digital insertion into the user's vagina. Such a tampon is formed by the process described below. In summary, the tampon is pressed axially into a split cavity mold while at least a portion of the tampon is maintained in the interior of a hollow mandrel. Thus, as shown in FIG. 2, the tampon 100 has an enlarged insertion portion 110. In a preferred embodiment, the tampon 100 also has a cover 160, longitudinal grooves 170 and longitudinal ribs 180.

Figure 3:
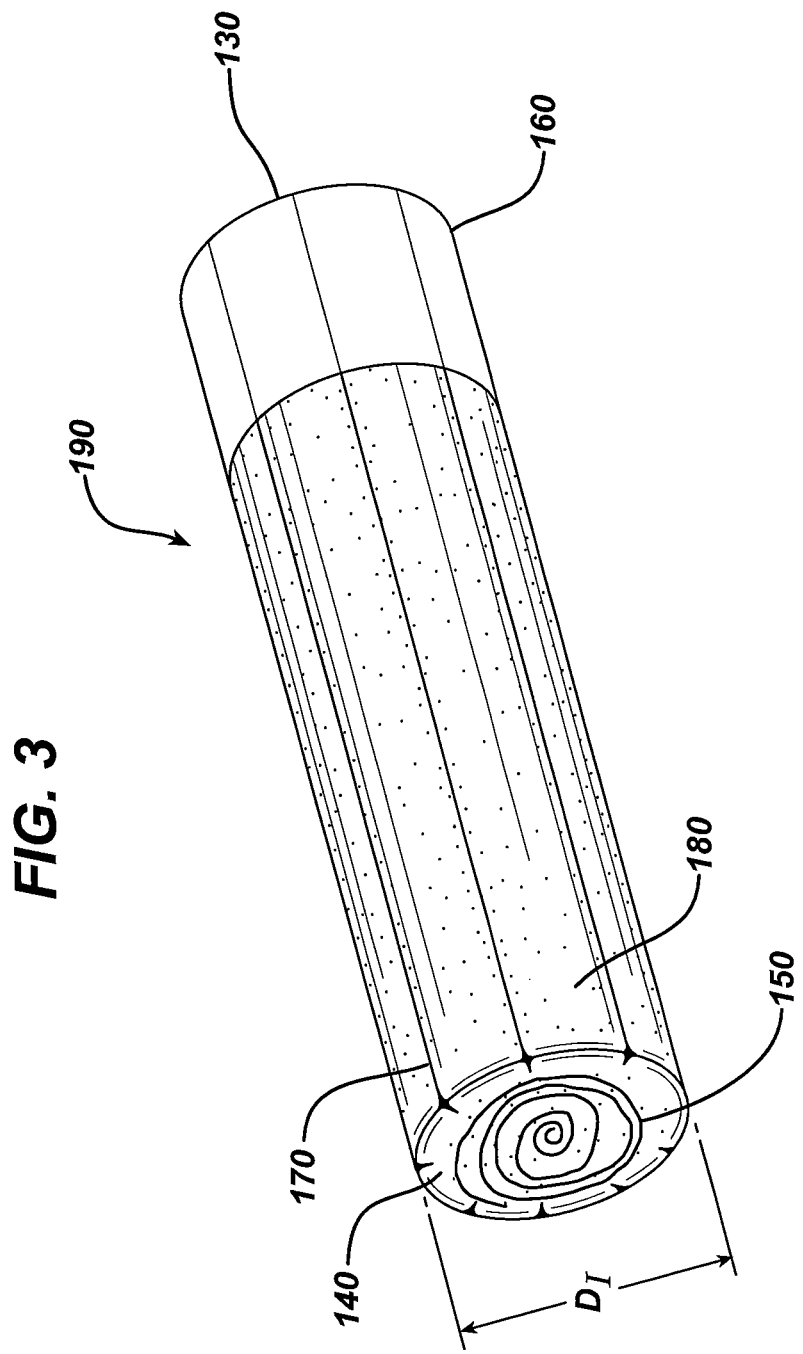
FIG. 3 is a perspective view of an intermediate pledget according to one embodiment of the present invention.

The tampon of FIG. 2 can be manufactured according to our new process. First, a conventional, radially compressed, dimensionally stable, substantially cylindrical intermediate pledget 190 having an intermediate pledget diameter $D_I$ (as shown in FIG. 3) can be made according to one or more Friese et al., U.S. Pat. No. 6,310,269, oriented helically about the outer surface as described in Schoelling, U.S. Pat. No. 8,735,647, or otherwise oriented along the length of the product, such as described in Fung et al., U.S. Pat. No. 8,460,262 B2; Kimball et al., U.S. Pat. Nos. 8,827,975 B2 and 8,834,439 B2; and Hysalma GmbH, EP Pat. No. 1 459 720 B1. the disclosures of which are herein incorporated by reference. Generally speaking, the intermediate pledget is formed by first obtaining a shaped mass of absorbent material called a tampon blank. This blank can be in the form of a roll of sheet-like material, a segment of a continuous absorbent material, a mass of randomly or substantially uniformly oriented absorbent material, an individually prepared or cast mass of absorbent material, and the like. The tampon blank is relatively uncompressed and has a relatively low density. It is then compressed to form the intermediate pledget having overall dimensions less than those of the blank prior to use. This intermediate pledget 190 is then further processed to provide the enlarged portion 110 shown in FIG. 2.

Figure 4:
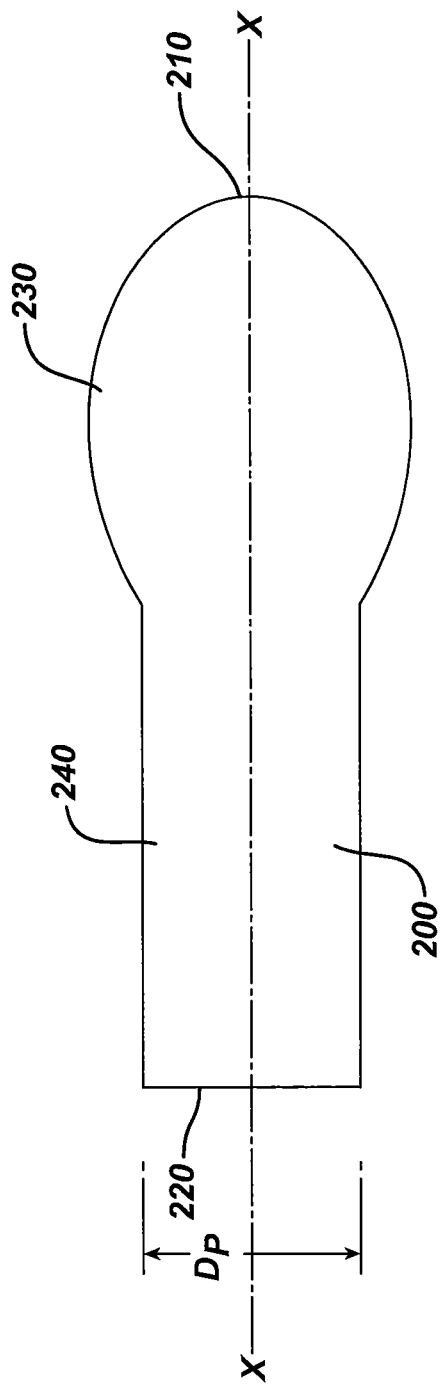
FIG. 4 is a side view of a primary tampon package according to one embodiment of the present invention.

In one embodiment of the process, a primary tampon package 200 having a length substantially greater than dimensions perpendicular thereto and defining a longitudinal axis X-X, a first closed end 210 and a second open end 220 is formed (FIG. 4). The primary tampon package 200 has a first portion 230, extending from the first, closed end and a second portion 240. This end may be closed as known to those of ordinary skill in the art. For example, a folded seal, such as four, or six or more folds about the end. More folds can better conform to a cylindrical shape. In addition, a curved flange seal may also be used. The second portion 240 of the primary tampon package 200 is substantially cylindrical with a substantially uniform diameter $D_P$ that is greater than the diameter $D_I$ of the intermediate pledget 190, while the first portion 230 is enlarged with respect to the second portion 240 along at least one dimension perpendicular to the longitudinal axis X-X.

Figure 5A:
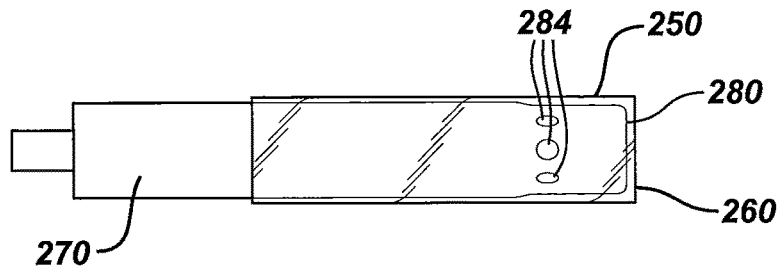
FIG. 5A is a side view of an intermediate primary tampon package disposed on a forming mandrel, prior to forming.
Figure 5B:
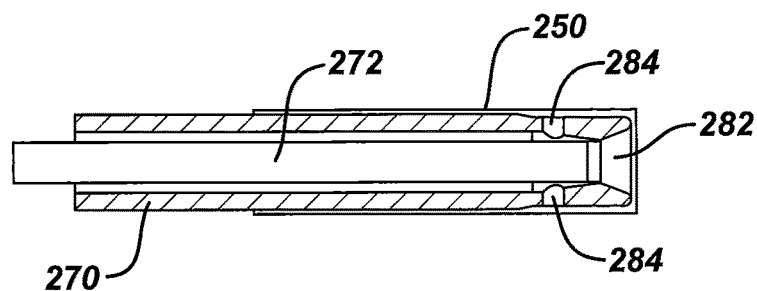
FIG. 5B is a cross-section of the intermediate primary tampon package disposed on a forming mandrel of FIG. 5A.
Figure 6A:
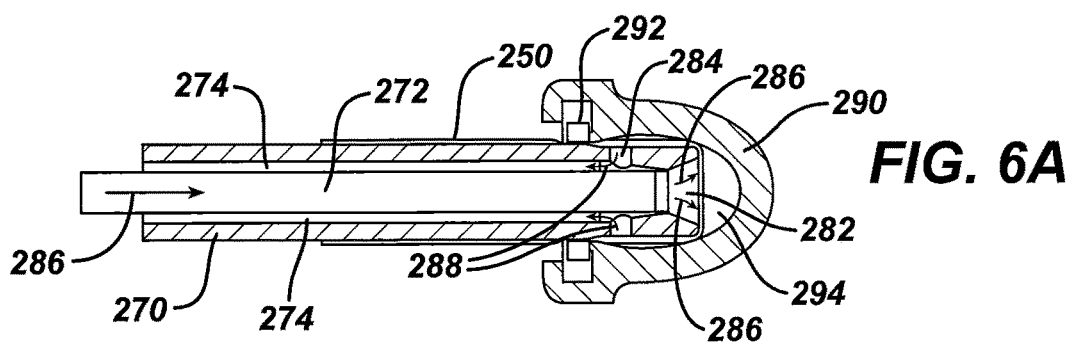
FIG. 6A is a side view of the intermediate primary tampon package on a forming mandrel in a package forming mold (in cross-section).
Figure 6B:
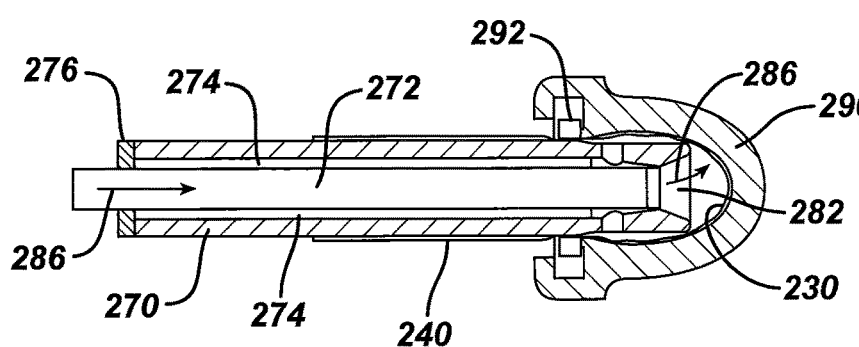
FIG. 6B is a side view of the intermediate primary tampon package of FIG. 6A on a forming mandrel expanded into the package forming mold (in cross-section).

In one embodiment, the primary tampon package 200 may be formed by wrapping a sheet of plastic wrapping material about a cylindrical mandrel, and sealing the sheet to form cylindrical tube. One end of the tube is closed and sealed, such that a cylindrical elongate primary tampon package intermediate having one open end results. As shown in FIGS. 5A and 5B, the intermediate primary tampon package 250 with the closed end 260 is then placed on a second hollow forming mandrel 270 with a forming end 280. The hollow forming mandrel 270 has a reduced diameter (in comparison to the majority of the forming mandrel) and an air delivery opening 282 at the forming end 280, an air delivery opening and air return openings 284 to permit air circulation as described below. As shown in FIG. 6A, the intermediate primary tampon package 250 and hollow forming mandrel 270 are placed in a mold 290 in a hot air thermoformer, which is closed by means of clamp 292 to isolate the forming chamber 294. Hot air is delivered through conduit 272 to the interior of the hollow forming mandrel 270 to the air delivery opening 282 inside the primary tampon package intermediate 250 (as shown by arrows 286) through the gap between the forming end 280 of the mandrel and is withdrawn through air return openings 284 and annulus 274 of hollow forming mandrel 270 (as shown by arrows 288) to soften the plastic material. As shown in FIG. 6B, the air flow from the annulus 274 is blocked (e.g., via plug 276 to pressurize the interior of the primary tampon package 250 to expand the closed end 260 of the package into the form of the mold 290, This produces the enlarged first portion 230 of the primary tampon package 200 proximate the first end thereof 210 as shown in FIGS. 4 and 7.

Figure 8:
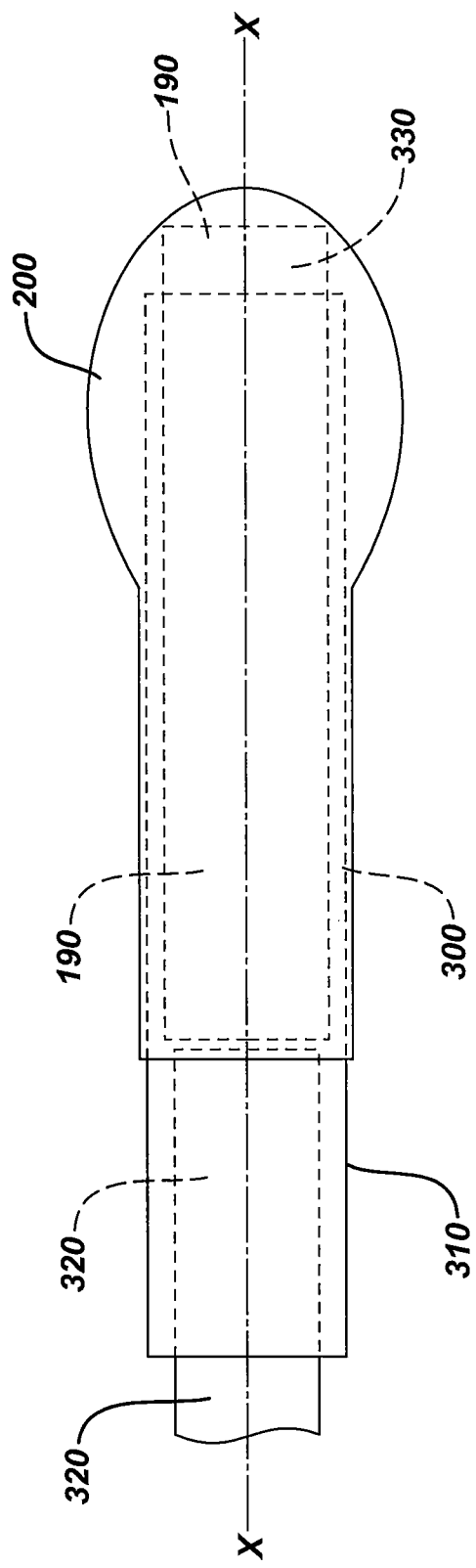
FIG. 8 is a side view of an assembly of a primary tampon package, an intermediate pledget, hollow mandrel carrier, and ram prior to placing the assembly into a tampon forming mold.
Figure 9:
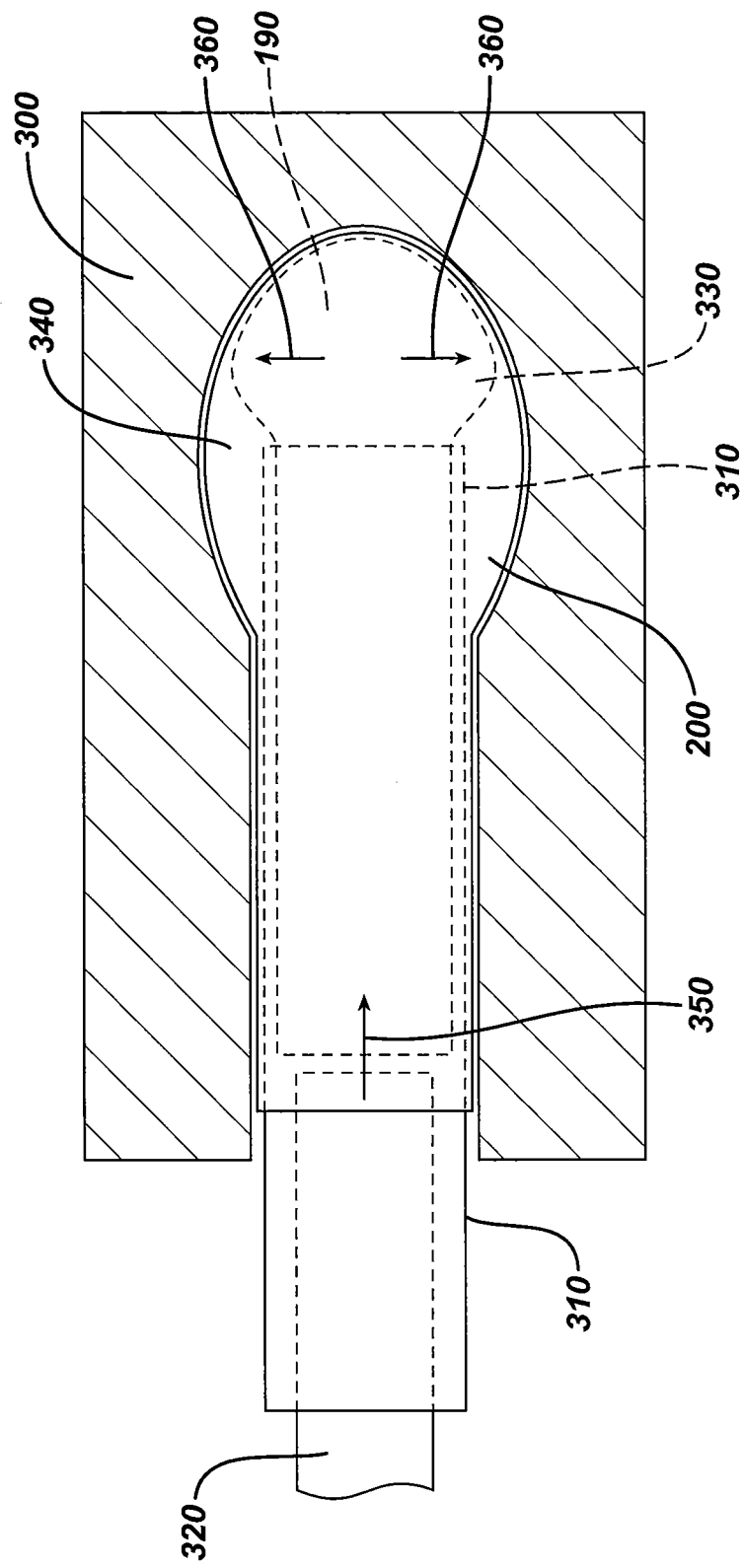
FIG. 9 represents a step in the inventive process and is a side view of the assembly of FIG. 8 located in the tampon forming mold (in cross-section) and axial force is applied to the base of the tampon.
Figure 10:
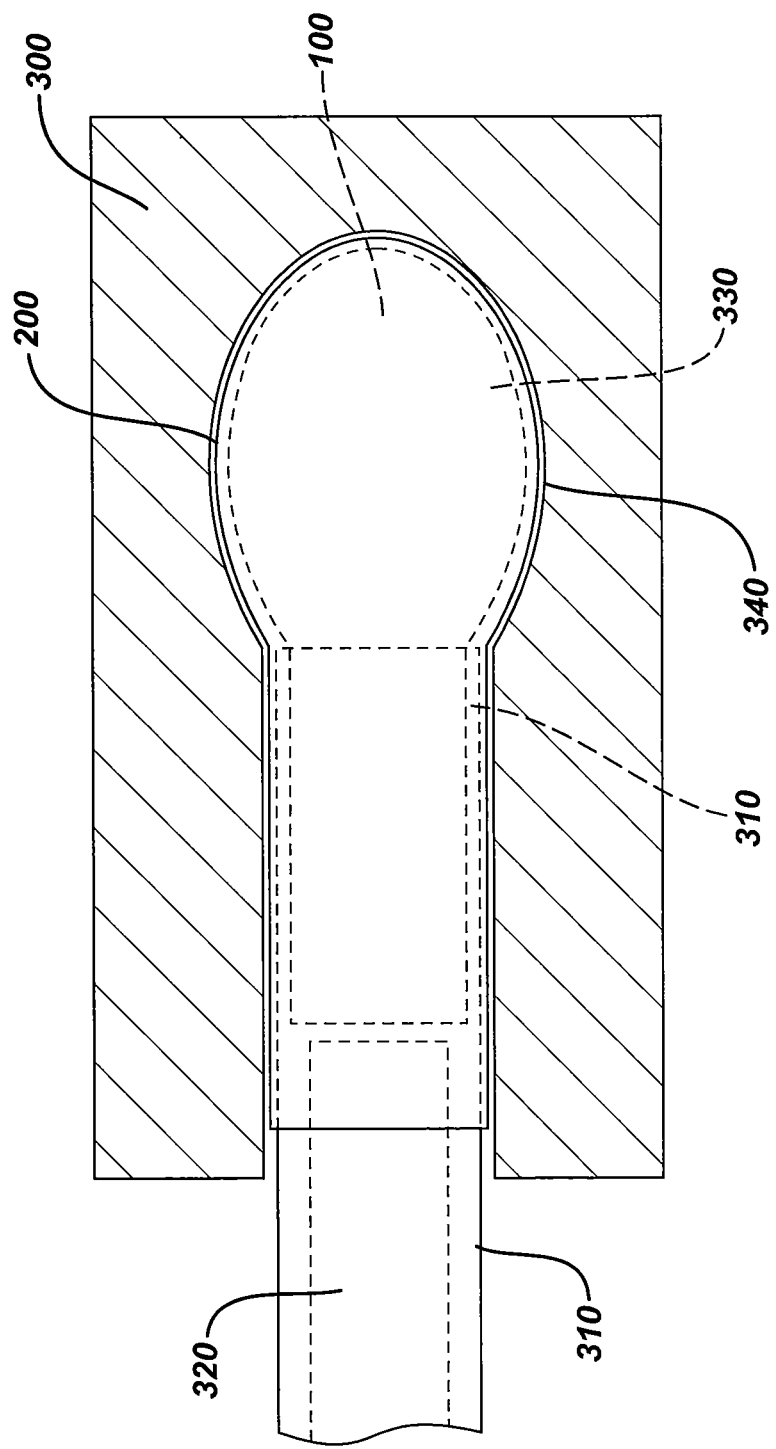
FIG. 10 represents a step in the inventive process and is a side view of the assembly of FIGS. 8-9 and the shaped, dimensionally stable tampon formed in the tampon forming mold (in cross-section).

To shape the intermediate tampon pledget 190 into the desired, dimensionally stable feminine hygiene tampon, an apparatus having a split cavity mold 300 substantially corresponding to the shape of the primary tampon package 200 is used. The substantially cylindrical intermediate tampon pledget 190 is placed in a hollow mandrel carrier 310, and the shaped primary tampon package 200 is placed over the carrier/intermediate tampon pledget 310/190 as shown in FIG. 8. The resulting assembly is placed in the split cavity mold 300, and a ram 320 is aligned with the intermediate tampon pledget 190 along the longitudinal axis X-X of the primary tampon package 200. The split cavity mold 300 is closed (either before or after the insertion of the assembly thereinto), and the tampon shaping process proceeds. As shown in FIG. 9, the hollow mandrel carrier 310 is withdrawn from about the intermediate tampon pledget 190 to expose increasing amounts of the end 330 of the pledget 190 in the enlarged portion 340 of the split cavity mold 300. As the hollow mandrel carrier 310 is withdrawn, the ram 320 applies force along the longitudinal axis X-X to force the exposed end 330 of the intermediate tampon pledget 190 against the split cavity mold 300. This axial force (represented by arrow 350) translates into a radial expansion (represented by arrows 360) of the exposed end 330 of the intermediate tampon pledget 190 to fill the enlarged volume 340 of the split cavity mold 300 and the primary tampon package 200. As the hollow mandrel carrier 310 continues to withdraw from the split cavity mold 300 and the ram 320 continues to force the intermediate tampon pledget 190 against the split cavity mold 300, the fibrous structure completes its expansion into the enlarged portion 330 of the split cavity mold 300 and the primary tampon package 200 (as shown in FIG. 10). Once the hollow mandrel carrier 310 has cleared the enlarged portion 330 of the split cavity mold 300, and the fibrous structure has filled the enlarged portion of the mold 330, the ram 320 stops its advance into the mold 300.

Figure 11:
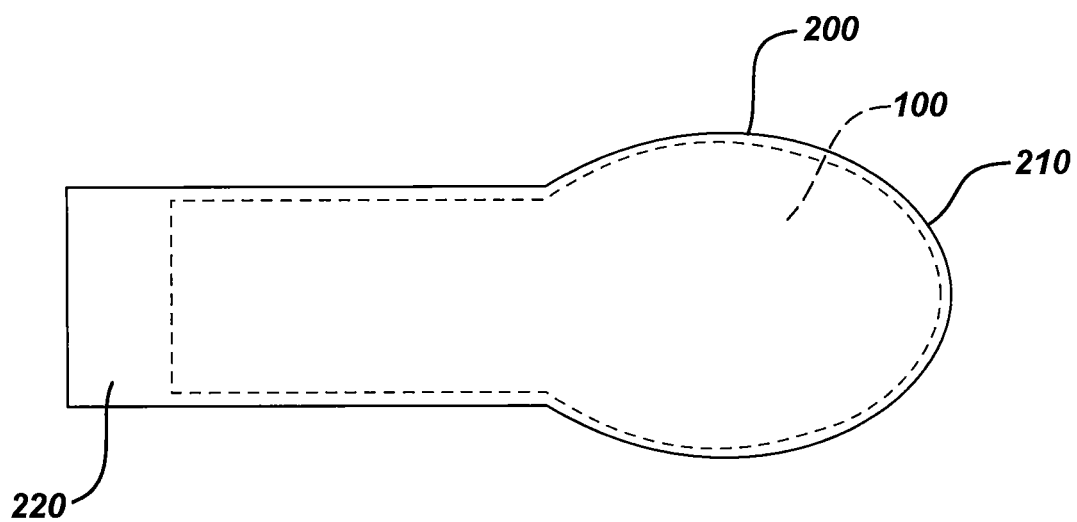
FIG. 11 is a side view of the shaped, dimensionally stable tampon formed in the primary tampon package, prior to closing the remaining open end thereof.
Figure 12:
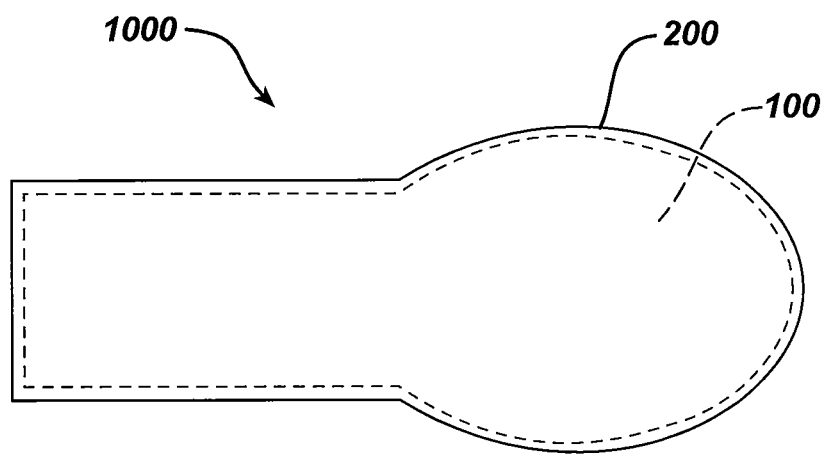
FIG. 12 is a side view of the final, packaged shaped product of FIGS. 5-11.

The hollow mandrel carrier 310 can be completely withdrawn from within the primary tampon package 200, and the split cavity mold 300 can be opened to permit removal of the shaped tampon 100 therefrom. Of course, the hollow mandrel carrier 310 may remain about the un-expanded portion of the tampon 100 to facilitate its removal from the mold 300. The open end 220 (as shown in FIG. 11) of the primary package 200 can then closed to provide the final, packaged shaped tampon product 1000 (as shown in FIG. 12). This end may be also closed as known to those of ordinary skill in the art. For example, a folded seal, as described above, a flange seal (optionally with a notch to enable the propagation of a tear to open the package. Alternatively, the primary tampon package may incorporate a reinforced tear strip.

Figure 13:
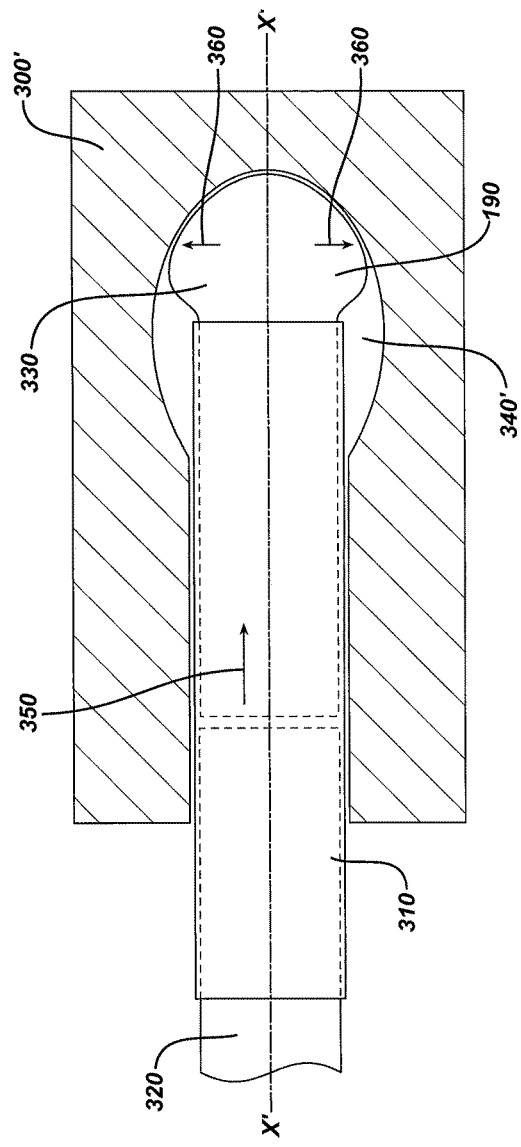
FIG. 13 represents a step in an alternative process and is a side view of an assembly of an intermediate pledget, hollow mandrel carrier, and ram located in the tampon forming mold (in cross-section) and axial force is applied to the base of the tampon.
Figure 14:
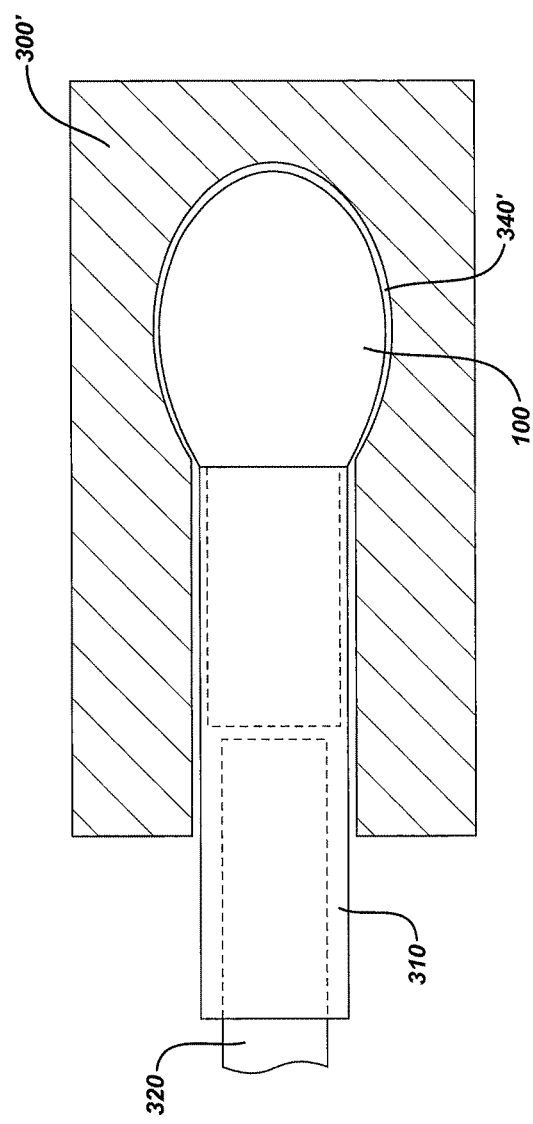
FIG. 14 represents a step in the process of FIG. 13 and is a side view of the assembly of FIG. 13 and the shaped, dimensionally stable tampon formed in the tampon forming mold (in cross-section).

In another embodiment of our process (shown in FIGS. 13 and 14), an apparatus having a split cavity mold 300' substantially corresponding to the shape of the desired finished tampon is used. As with the previous embodiment, the substantially cylindrical intermediate tampon pledget 190 is placed in a hollow mandrel carrier 310. However, only the hollow mandrel carrier 310 and substantially cylindrical intermediate tampon pledget 190 form the assembly that is placed in the split cavity mold 300', and a ram 320 is aligned with the intermediate tampon pledget 190 along the longitudinal axis X'-X' of the intermediate tampon pledget 190. The split cavity mold 300' is closed (either before or after the insertion of the assembly thereinto), and the tampon shaping process proceeds. The hollow mandrel carrier 310 is withdrawn from about the intermediate tampon pledget 190 to expose increasing amounts of the end 330 of the pledget in the enlarged portion 340' of the split cavity mold 300'. As the hollow mandrel carrier 310 is withdrawn, the ram 320 applies force along the longitudinal axis X'-X' to force the exposed end 330 of the intermediate tampon pledget 190 against the split cavity mold 300'. This axial force (represented by arrow 350) translates into a radial expansion (represented by arrows 360) of the exposed end 330 of the intermediate tampon pledget 190 to fill the enlarged volume 340' of the split cavity mold 300'. Once the hollow mandrel carrier 310 has cleared the enlarged portion of 340' the split cavity mold 300', and the fibrous structure has filled the enlarged portion 340' of the mold 300', the ram 320 stops its advance into the mold 300'. The hollow mandrel carrier 310 can be completely withdrawn from within the split cavity mold 300', which can be opened to permit removal of the shaped tampon 100 therefrom. Of course, the hollow mandrel carrier 310 may remain about the un-expanded portion of the tampon 100 to facilitate the removal from the mold 300'. The shaped tampon 100 can then be enclosed within a primary tampon package which may be previously shaped to accommodate the finished tampon or it may be formed about the finished tampon, e.g., by shrink wrapping (as shown in FIG. 12 for the previous embodiment).

Figure 15A:
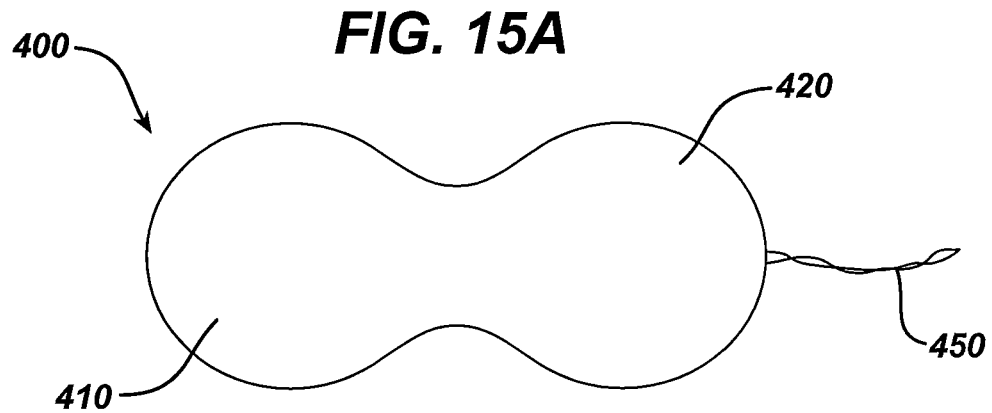
FIGS. 15A-C are side representations of alternative tampon shapes.

While the tampons have been described above with respect to a tampon having an enlarged end, especially an enlarged insertion end, alternative embodiments are also contemplated, including a tampon 400 that has two enlarged ends 410, 420, and a withdrawal string 450 (FIG. 15A); a tampon 500 that has two compressed ends 510, 520, an enlarged central portion 530, and a withdrawal string 550

Figure 15B:
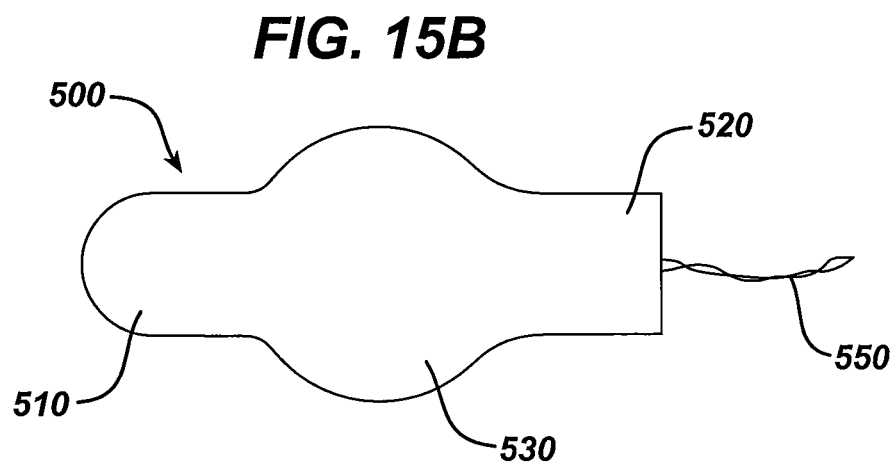
Figure 15C:
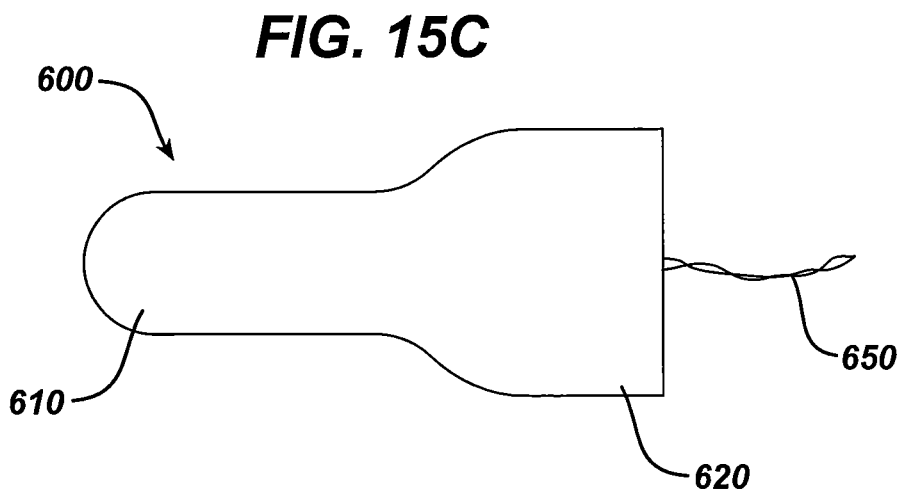

(FIG. 15B); and a tampon 600 that has a compressed insertion end 610, and expanded withdrawal end 620, and a withdrawal string 650 (FIG. 15C); and the like. These embodiments would require modified split cavity molds that provide the desired shape. In addition, the embodiment of FIG. 15C may require a second ram with cross-sectional dimensions that correspond to the withdrawal end dimensions.

Figure 16A:
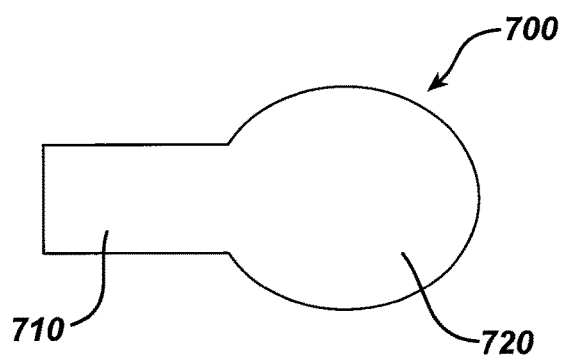
FIG. 16A is a top plan view of an alternative tampon shape.
Figure 16C:
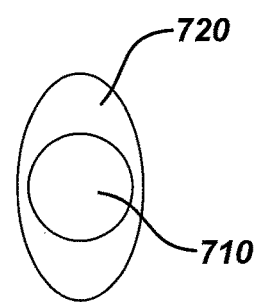
FIG. 16C is an end view of the tampon of FIGS. 16A-B showing an ovate cross-section of the enlarged portion.
Figure 16B:
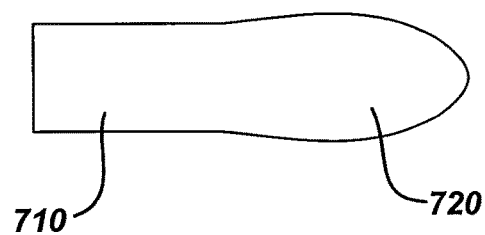
FIG. 16B is a side elevation of the tampon of FIG. 16A.
Figure 17A:
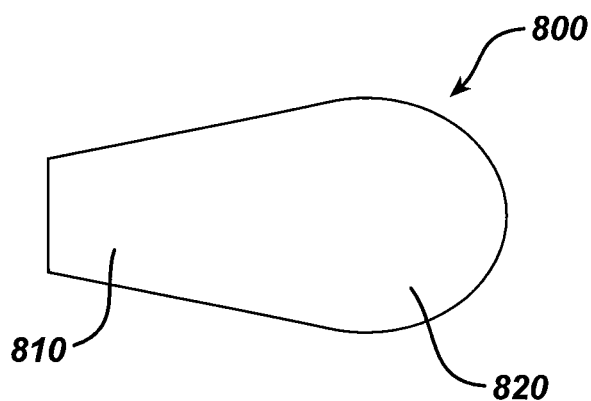
FIG. 17A is a top plan view of an alternative tampon shape.
Figure 17C:
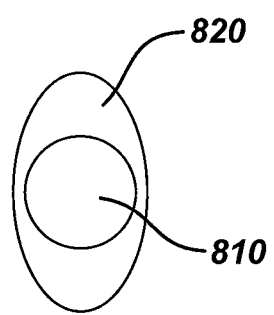
FIG. 17C is an end view of the tampon of FIGS. 17A-B showing an ovate cross-section of the enlarged portion.
Figure 17B:
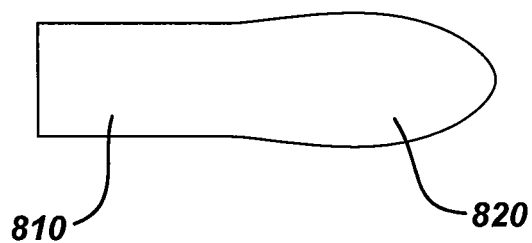
FIG. 17B is a side elevation of the tampon of FIG. 17A.

In addition, the cross-section of the finished tampon may be cylindrical or other desired shapes. For example, a tampon 700 having differing cross-sectional shapes is shown in FIG. 16. The cross-section of a compressed portion 710 of the finished tampon 700 may be substantially cylindrical, while the cross-section of an enlarged portion 720 may be more oval as shown in FIG. 16A-C. In an alternative embodiment, a tampon 800 having differing cross-sectional shapes is shown in FIG. 17. The cross-section of a compressed portion 810 of the finished tampon 800 may be tapered from cylindrical to oval, while the cross-section of an enlarged portion 820 may be more oval as shown in FIG. 17A-C.

As the tampon is formed by pressing an intermediate pledget is pressed axially into a split cavity mold while at least a portion of the tampon is maintained in the interior of a hollow mandrel. This results in the radial expansion into the split cavity mold, as described above. The intermediate pledget is longer than the finished tampon. In one embodiment, the finished tampon has a length of between about 80% and about 95% of the length of the intermediate pledget from which it is formed. Preferably, in this embodiment, the finished tampon has a length of between about 90% of the length of the intermediate pledget from which it is formed.

Depending upon the volume of the cavity of the split cavity mold and the axial force on the intermediate pledget, the fiber density of the finished tampon may be substantially similar to that of the intermediate pledget from which it is formed, or it may be different. One of ordinary skill in the art will know to adjust the forces and volumes to achieve a desired fiber density in the enlarged portion of the finished tampon. As used in the specification and the claims, the term "fiber density" and variants thereof relate to the relative proportion of fibers to void space in a given volume of the fibrous structure.

In one preferred embodiment, the split cavity mold used in forming the shaped tampon from the intermediate pledget is operated at ambient conditions. In alternate embodiments, depending upon the material used in the process, there may be a benefit to addition sufficient heat to set the fibers in the enlarged shape.

EXAMPLES

The present invention will be further understood by reference to the following specific Examples that are illustrative of the composition, form and method of producing the device of the present invention. It is to be understood that many variations of composition, form and method of producing the device would be apparent to those skilled in the art. The following Examples, wherein parts and percentages are by weight unless otherwise indicated, are only illustrative.

Example 1

Ten regular absorbency o.b.® tampons (having a nonwoven fabric cover) similar to those available from Energizer Holdings, Ltd. were made in a hand press, and they were shaped into a wrapper having an enlarged end as described above. The corresponding regular absorbency o.b.® tampons generally have a column strength in the range of about 30 to 40 Newtons (N). The resulting products were tested for column strength as described below. The dimensions and column strength are provided in Table 1, below.

TABLE 1

|  | Mean | Standard Dev. | Minimum | Maximum |
| --- | --- | --- | --- | --- |
| Weight (g) | 3.12 | 0.02 | 3.07 | 3.14 |
| Small diameter (mm) | 15.55 | 0.18 | 15.32 | 15.88 |
| Large diameter (mm) | 16.52 | 0.28 | 16.16 | 17.10 |
| Length (mm) | 50.3 | 1.0 | 48.6 | 51.8 |
| Column Strength (N) | 40.7 | 4.7 | 34.1 | 47.6 |

The test results show that this product maintains user insertion requirements for digital tampons. It was surprising to learn the product column strength was not significantly weakened by the non-cylindrical shape.

Column Strength Test: A tampon is stressed in the compression mode until it loses its rigidity, and the resulting force necessary to establish this point is determined.
1.0 Precision and Accuracy:
1.1 Load Cell±1% of applied force
1.2 Load Frame Speed and Displacement±1%
1.3 Balance precision±0.01 g
2.0 Equipment:
2.1 Tensiometer, Instron or equivalent.
2.2 Calibrated load cell capable of measuring at least 100N (Compression).
2.3 Bluehill software or equivalent.
2.4 Template holder, see drawings in section 15.5.
3.0 Sample Preparation: None
4.0 Operating Conditions:
4.1 The Tensiometer must be set up to include the following parameters:
  Test Parameters
    Test speed 700 mm/min
  Informational Parameters
    Data Rate 20 Hz
    Break sensitivity (optional) 3.5%
    Distance traveled 3 cm
    Modulus (Young's tensile stress) 0.5 mm to 16 mm
    Yield off set (Young's Tensile Stress) 0.8 mm
5.0 Procedure:
5.1 Attach the template holders to the tensiometer. Set the distance between the sample holders to 3.5 inches. Tare the distance.
5.2 Place the appropriate templates in the template holders for the format that is to be tested. Lock the top template holder in place with the screw.
5.3 Tare (zero) the force on the tensiometer.
5.4 Unwrap tampon and unfold the string.
5.5 Weight and place the tampon dome on top on the bottom plate. Be sure that the tampon is placed vertically.
5.6 Start the tensiometer. The crosshead will move downwards at a speed of 700 mm for a maximum of 3 cm or until the tampon "breaks".
5.6.1 The "break" point will automatically be recognized by the software. The load frame will return to the start position.

5.6.2 If the "break" point is not recognized, the test will run the full course before stopping and returning to the start position. The maximum force can then be read by pointing the cursor at the break point on the graph and recording the value from the screen.

5.6 Repeat 5.3 to 5.5 for the remaining tampons.

5.7 All results will be printed, initialed and dated for each lot.

Example 2

Ten regular absorbency o.b.® tampons (having a nonwoven fabric cover) similar to those available from Energizer Holdings, Ltd. were made in a hand press, and they were shaped into a wrapper having an enlarged end as described above. The resulting products were tested for absorbency according to the Syngina Test as described in 21 CFR part 801, subpart H, Sec. 801.430(f)(2) [Revised as of Apr. 1, 2014]. The corresponding regular absorbency o.b.® tampons generally have an absorbency in the range of 12 to 15 grams (g). The dimensions and absorbency of the inventive tampons are provided in Table 2 below.

TABLE 2

|  | Mean | Standard Dev. | Minimum | Maximum |
| --- | --- | --- | --- | --- |
| Weight (g) | 3.11 | 0.03 | 3.04 | 3.13 |
| Small diameter (mm) | 15.80 | 0.16 | 15.60 | 16.00 |
| Large diameter (mm) | 16.58 | 0.18 | 16.30 | 16.90 |
| Length (mm) | 50.0 | 0.65 | 49.3 | 51.3 |
| Absorbency (g) | 15.2 | 0.49 | 14.4 | 16.1 |

The tests results show that the absorbency is unexpectedly at or above the upper end of the range for cylindrical products of equal weight.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A process of forming a shaped, dimensionally stable tampon comprising the steps of:
    a. radially compressing a tampon blank to form a dimensionally stable intermediate pledget having an intermediate pledget diameter and a longitudinal axis;
    b. placing the intermediate pledget into a hollow carrier;
    c. inserting the intermediate pledget and hollow carrier into a mold having a shape corresponding to a desired final tampon shape, wherein the desired final tampon shape has a maximum dimension perpendicular to the longitudinal axis that is greater than the largest diameter of the intermediate pledget, wherein the mold has an access opening through which the hollow carrier can be withdrawn;
    d. urging the intermediate pledget into the mold via a ram bearing on an end of the intermediate pledget contained within the hollow carrier and withdrawing the hollow carrier from the mold such that an exposed end of the intermediate pledget is forced against the mold whereby axial force on the intermediate pledget provides radial expansion from the longitudinal axis of the intermediate pledget to permit the exposed end of the intermediate pledget to substantially fill the mold and to form the shaped, dimensionally stable tampon;
    e. removing the shaped, dimensionally stable tampon from the mold; and
    f. enclosing the shaped, dimensionally stable tampon in a primary package that conforms to the shape thereof.

2. The process of claim 1 wherein the mold is a split cavity mold.

3. The process of claim 1 wherein the enlarged portion of the mold has a circular cross-section, perpendicular to the longitudinal axis of the intermediate pledget.

4. The process of claim 1 wherein the enlarged portion of the mold has an ovate cross-section, perpendicular to the longitudinal axis of the intermediate pledget.

5. The process of claim 1 wherein the enlarged portion of the mold corresponds to the insertion end of the tampon.

6. The process of claim 1 wherein the enlarged portion of the mold corresponds to a central portion of the tampon.

7. The process of claim 1 wherein the enlarged portion of the mold comprises a plurality of enlarged regions.

8. The process of claim 7 wherein one enlarged portion is disposed at a first end of the mold cavity, corresponding to the insertion end of the tampon and another enlarged portion is disposed at a second end of the mold cavity, corresponding to the withdrawal end of the tampon.

* * * * *